United States Patent [19]

Buendia et al.

[11] Patent Number: 5,622,915
[45] Date of Patent: Apr. 22, 1997

[54] METHOD OF USING TRICLOPYR TO INCREASE FRUIT SIZE OR QUALITY OR MATURATION RATE

[75] Inventors: Jose Buendia, Madrid; Rafael Molina, Murcia; Jose L. P. Gil, Valencia, all of Spain

[73] Assignee: DowElanco, Indianapolis, Ind.

[21] Appl. No.: 392,832

[22] PCT Filed: Jul. 5, 1994

[86] PCT No.: PCT/US94/07526

§ 371 Date: Jun. 8, 1995

§ 102(e) Date: Jun. 8, 1995

[87] PCT Pub. No.: WO95/01725

PCT Pub. Date: Jan. 19, 1995

[30] Foreign Application Priority Data

Jul. 5, 1993 [GB] United Kingdom ............... 9313838

[51] Int. Cl.$^6$ ........................................... A01N 43/40
[52] U.S. Cl. ............................................. 504/254
[58] Field of Search ............................... 504/254

[56] References Cited

FOREIGN PATENT DOCUMENTS

| 55-100306 | 7/1980 | Japan . |
| 55-100307 | 7/1980 | Japan . |

OTHER PUBLICATIONS

C.D. Forgie et al., "Blackberry Control with Triclopyr," Proc, 30th N.Z. Weed and Pest Control. Conf. (1977).
Nishiyama et al. JPOABS abstract of JP 55–100306, 1980.
Nishiyama et al. JPOABS abstract of JP 55–100307, 1980.

*Primary Examiner*—S. Mark Clardy
*Attorney, Agent, or Firm*—Donald R. Stuart

[57] ABSTRACT

A method for regulating plant growth which comprises applying to a fruit bearing plant an amount of 3,5,6-trichloro-2-pyridyloxyacetic acid (i.e., triclopyr) or a lower ($C_{1-10}$) alkyl ester or salt thereof that is nonphytotoxic and effective to provide increased fruit size or quality or faster maturation without causing significant (>25%) thinning.

8 Claims, No Drawings

METHOD OF USING TRICLOPYR TO INCREASE FRUIT SIZE OR QUALITY OR MATURATION RATE

This application has been filed under 35 USC 371 from international application PCT/US94/07526, filed Jul. 5, 1994.

This invention relates to methods for regulating plant growth and enhancing fruit production by application of 3,5,6-trichloro-2-pyridyloxyacetic acid or an ester or a salt thereof to a fruit bearing plant.

3,5,6-trichloro-2-pyridyloxyacetic acid, also known as triclopyr, is a well known herbicide for woody plants. Methods of preparing triclopyr and lower alkyl esters thereof are disclosed in, for example, U.S. Pat. Nos. 3,862, 952, 4,127,582, and 4,701,531.

Use of triclopyr as a thinning agent for mandarin orange is disclosed in Japanese patent application Kokai No. 80/100307.

The invention provides a method for regulating plant growth which comprises applying to a fruit bearing plant an amount of 3,5,6-trichloro-dyloxyacetic acid or a lower ($C_{1-10}$) alkyl ester or salt thereof that is nonphytotoxic and effective to provide increased fruit size or quality or faster maturation without causing significant thinning.

A preferred embodiment of the invention is application of triclopyr to citrus, pome, or stone fruit trees in an amount that is both nonphytotoxic and effective to enhance fruit size.

A particularly preferred embodiment of the invention is use of triclopyr in controlling development of citrus fruit.

As used herein, the term "nonphytotoxic" means not significantly toxic to the plant.

The preferred method of application is as a medium to high volume overall spray to the fruit bearing plant. The application race is in the range from about 10g/ha to about 50 g/ha. In a preferred embodiment, a solution containing 5–15 ppm of triclopyr in water is applied to fruit trees at a race of about 1000 to about 2500 L/ha.

The preferred active ingredient is triclopyr acid, however lower alkyl esters (for example $C_{1-10}$, generally $C_{1-4}$ esters) and salts of triclopyr may also be used.

The preferred formulation is a water dispersible tablet formed by compressing a mixture comprising 10 percent by weight of triclopyr acid and 90 percent by weight of tablet binder.

Timing of application is critical to avoiding thinning. As used herein, the term "significant thinning" means thinning that results in a yield loss greater than 25 percent (where yield refers to the number of fruit). Significant thinning can result if an application is made before the fruit has reached an appropriate growth stage. In general, the higher the rate and the sooner the application, the greater the danger of experiencing significant thinning. In citrus, the appropriate time for application is at the early stage of fruit growth (20–30 mm fruit diameter). The ideal application rate and timing varies somewhat by species, but can be determined by routine experimentation.

For lemons, applying triclopyr at a rate of about 37.5 g/ha when the lemons have an average diameter of about 22–28 mm gives maximum increase in fruit size and advances harvest by approximately one month. The size range 22–28 mm is important. If the lemons are smaller than 22 mm they are likely to drop, and if larger than 28 mm hey will receive less than optimum stimulation. When flowering is homogeneous, one application at the 37.5 g/ha is sufficient. When the flowering period is long, two applications at half that rate about 10 to 15 days apart may be used.

Spanish lemons are harvested when the fruit has a diameter of about 56 mm. There are typically three harvests per season. In plots treated with 37.5 g/ha of triclopyr here are typically twice as many lemons harvested at the first collection than in similar control plots. Lemons can be harvested two to three weeks earlier. Yield increases of about 10 percent have been observed. The quality of treated lemons including colour, pulp, and rate of decomposition after storage in freeze houses, is not adversely effected by the treatment. The peel thickness is generally reduced, and there is a tendency to reduce the amount of acidity, thereby producing sweeter lemons.

For grapefruit, the recommended application rate is again 37.5 g/ha. At the time of application, the grapefruit should be about 22–28 mm in diameter. When treated in accordance with these recommendations, average fruit weight has shown a statistically significant increase of 12 to 33 percent compared to untreated controls. Measurement of colour indicates an increase of the red colour in the peel, pulp, and juice in the variety Star Ruby. Preliminary data indicates that the content of hesperidine, the substance which gives the sour taste in grapefruits, is reduced. The peel thickness of treated grapefruit is reduced. Application rates in the range from 12.5 g/ha to 50 g/ha have all been found to produce some thinning in grapefruit. No other adverse results have been noted.

For mandarins, including tangerines and hybrids, the recommended application rate is 25 to 37.5 g/ha. At the time of application, the mandarins should be 22–26 mm in diameter. Application rates at the upper end of the 25–37.5 g/ha range are appropriate when the fruit has reached a size at the upper end of the 22–26 mm range. Mandarins are sensitive for thinning, and treatment before the fruit reaches 18 mm in diameter can lead to 40 to 50 percent thinning. After the fruit reaches 22 mm, treatment at the 37.5 g/ha rate may produce from 5 to 20 percent thinning, depending primarily on diameter variability of the fruit at the time of application. At the recommended rates of 25 to 37.5 g/ha a statistically significant average size increase of 7 to 14 percent has been observed. More significantly, in comparison to untreated plots, there are more fruits in Class I (greater than 63 mm) and Class II (58–63 mm) and less fruits below 48 mm where there is no commercial value. Treatment also decreases acidity content and increases sugar content, providing advanced maturity. Ripening occurs ten days sooner as a result of treatment. In addition, treatment in accordance with the invention provides colour improvement in most varieties and improvement in the peel quality, e.g. less cold pitting and less fruit splitting.

A slightly lower application rate is appropriate for oranges. Triclopyr applied at rates of 18.75 to 25 g/ha has been found to produce maximum size increase without producing any undesirable effects. Application rates of 50 to 75 g/ha may produce shrinking of the Emits and consequent yield reduction; on the other hand the higher application rates afford some residual effect the following year. At the time of application, the oranges should be 25 to 30 mm in diameter.

Triclopyr applied to oranges of the variety Navelate at the rate of 18.75 g/ha in July when the fruit was 25 to 30 mm in diameter increased fruit size and yield by 7 to 12 percent. There was also a reduction in peel thickness, reduction of acidity, and increase of colour.

It has also been found that an additional application of triclopyr at a rate of approximately 12.5 to 25 g/ha when the oranges turn from green to yellow (November) gives excellent control of preharvest fruit drop.

In general, the plant response is believed to be hormonal as demonstrated by the balance of an increased number and larger cells produced in the fruit.

Within a significant window of application timing and application rate, there are no evident phytotoxic effects.

We claim:

1. A method for regulating plant growth which comprises applying to a fruit bearing plant 3,5,6-trichloro-2-pyridyloxyacetic acid or a $C_{1-10}$ alkyl ester or salt thereof at an application rate that is nonphytotoxic and effective to provide increased fruit size or quality or faster maturation, and at a time when the plant is bearing sufficiently mature fruit so that significant thinning does not occur.

2. A method as claimed in claim 1 wherein the fruit bearing plant is a citrus tree bearing fruit having a diameter of from 20 to 30 mm.

3. A method as claimed in claim 1, wherein the fruit bearing plant is a grapefruit or lemon tree, bearing fruit with a diameter of from 22 to 28 mm.

4. A method as claimed in claim 1, wherein the fruit bearing plant is a mandarin tree, bearing fruit with a diameter of from 22 to 26 mm.

5. A method as claimed in claim 1 wherein the application rate is from 10 g/ha to 50 g/ha.

6. A method as claimed in claim 5, wherein the application rate is from 20 to 40 g/ha.

7. A method as claimed in claim 6, wherein the application rate is about 37.5 g/ha.

8. A method as claimed in claim 1, wherein a solution containing from 5 ppm to 15 ppm of 3,5,6-trichloro-2-pyridyloxyacetic acid in water is applied to fruit trees at a rate of from 1000 to 2500 L/ha.

* * * * *